US012171527B2

(12) United States Patent
Chang et al.

(10) Patent No.: US 12,171,527 B2
(45) Date of Patent: Dec. 24, 2024

(54) EAR THERMOMETER CAPABLE OF IDENTIFYING INFRARED TRANSMITTANCE OF PROBE COVER

(71) Applicant: RADIANT INNOVATION INC., Hsinchu County (TW)

(72) Inventors: Yung-Chang Chang, Hsinchu County (TW); Tseng-Lung Lin, Hsinchu County (TW); An-Chin Lai, Taichung (TW)

(73) Assignee: RADIANT INNOVATION INC., Hsinchu County (TW)

( * ) Notice: Subject to any disclaimer, the term of this patent is extended or adjusted under 35 U.S.C. 154(b) by 804 days.

(21) Appl. No.: 17/226,024

(22) Filed: Apr. 8, 2021

(65) Prior Publication Data

US 2022/0322949 A1    Oct. 13, 2022

(51) Int. Cl.
*A61B 5/01*    (2006.01)

(52) U.S. Cl.
CPC ........ *A61B 5/01* (2013.01); *A61B 2560/0233* (2013.01); *A61B 2560/0475* (2013.01); *A61B 2562/0271* (2013.01); *A61B 2562/247* (2013.01)

(58) Field of Classification Search
CPC ............. A61B 5/01; A61B 2560/0233; A61B 2560/0475; A61B 2562/0271; A61B 2562/247; A61B 2560/0238; A61B 5/6817
See application file for complete search history.

(56) References Cited

U.S. PATENT DOCUMENTS

2006/0120432 A1\* 6/2006 Lantz ................. G01J 5/049
374/E1.013

FOREIGN PATENT DOCUMENTS

CN    112504478 A  \*  3/2021  ............. G01J 5/027
JP    2001327473 A  \*  11/2001

OTHER PUBLICATIONS

Machine-generated English translation of Zhang et al. (CN 112504478 A) (Year: 2023).\*
Machine-generated English translation of JP 2001-327473 A (Year: 2024).\*

\* cited by examiner

*Primary Examiner* — Pascal M Bui Pho
*Assistant Examiner* — Taylor Deutsch
(74) *Attorney, Agent, or Firm* — Li & Cai Intellectual Property Office

(57) ABSTRACT

An ear thermometer capable of identifying an infrared transmittance of a probe cover is provided and includes an ear thermometer body, a probe, and a plurality of activation elements. The probe is disposed on the ear thermometer body. A closed end of the probe cover is used for infrared transmittance, and the probe cover has different infrared transmittances according to a thickness variation thereof. The activation elements are disposed on the ear thermometer body and configured to detect the infrared transmittance of the probe cover. Each of the activation elements includes an ON state and an OFF state so that the activation elements are arranged to form different sensor combinations, which respectively correspond to different infrared transmittances, and any two of the different sensor combinations have the two corresponding infrared transmittances that are different from one another.

14 Claims, 12 Drawing Sheets

EAR THERMOMETER CAPABLE OF IDENTIFYING INFRARED TRANSMITTANCE OF PROBE COVER

FIELD OF THE DISCLOSURE

The present disclosure relates to an ear thermometer, and more particularly to an ear thermometer capable of identifying an infrared transmittance of a probe cover.

BACKGROUND OF THE DISCLOSURE

Conventionally, ear or forehead thermometers are used as body temperature measuring devices to sense a temperature of a human body. However, due to an increased awareness of health and safety, a disposable ear cap is usually placed onto a probe of the ear thermometer before measuring an ear temperature. Generally speaking, a thickness of a top portion of the ear cap is relevant to an infrared transmittance of the ear cap. Therefore, when a user places ear caps of different thicknesses on the ear thermometer, an accuracy of the ear temperature that is measured by the ear thermometer is affected. To prevent the ear caps from inconsistencies in terms of thickness, manufacturers generally utilize a sifting process to sell the ear caps whose thickness deviations are within a specific range, and throw away those that exceed a tolerance. In the current manufacturing process, there are up to 30% to 40% of the ear caps that need to be thrown away for exceeding the tolerance.

Therefore, by labeling and grouping the ear caps of different thicknesses during the sifting process and by having an improved structural design, how a recognition rate of the infrared transmittance of the ear cap can be increased to overcome the above-mentioned problems has become one of the important issues to be solved in this field.

SUMMARY OF THE DISCLOSURE

In response to the above-referenced technical inadequacies, the present disclosure provides an ear thermometer capable of identifying an infrared transmittance of a probe cover.

In one aspect, the present disclosure provides an ear thermometer capable of identifying an infrared transmittance of a probe cover. The ear thermometer includes an ear thermometer body, a probe, a plurality of activation elements, and an infrared detection element. The probe is disposed on the ear thermometer body and allows the probe cover to be placed thereon for infrared transmittance. The probe cover has a closed end and different infrared transmittances according to thickness variations of the closed end. The activation elements are disposed on the ear thermometer body and adjacent to the probe, and the activation elements are configured to detect the infrared transmittance of the probe cover. Each of the activation elements includes an ON state and an OFF state so that the activation elements are arranged to form a plurality of different sensor combinations. The different sensor combinations respectively correspond to different infrared transmittances, and any two of the different sensor combinations have the two corresponding infrared transmittances that are different from one another. The infrared detection element is disposed in the ear thermometer body, the infrared ray passes through the probe cover and enters the ear thermometer body through the probe, and the infrared detection element receives the infrared ray and outputs a detection signal.

One of the beneficial effects of the present disclosure is that, in the ear thermometer capable of identifying the infrared transmittance of the probe cover provided herein, through the technical solutions of "the plurality of activation elements being disposed on the ear thermometer body and being able to detect the infrared transmittance of the probe cover" and "each of the activation elements including the ON state and the OFF state so that the activation elements being arranged to form a plurality of different sensor combinations, and the different sensor combinations respectively corresponding to a plurality of different infrared transmittances", the ear thermometer can quickly identify the infrared transmittance of the probe cover that is placed thereon.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which.

DETAILED DESCRIPTION OF THE EXEMPLARY EMBODIMENTS

Figure 1:
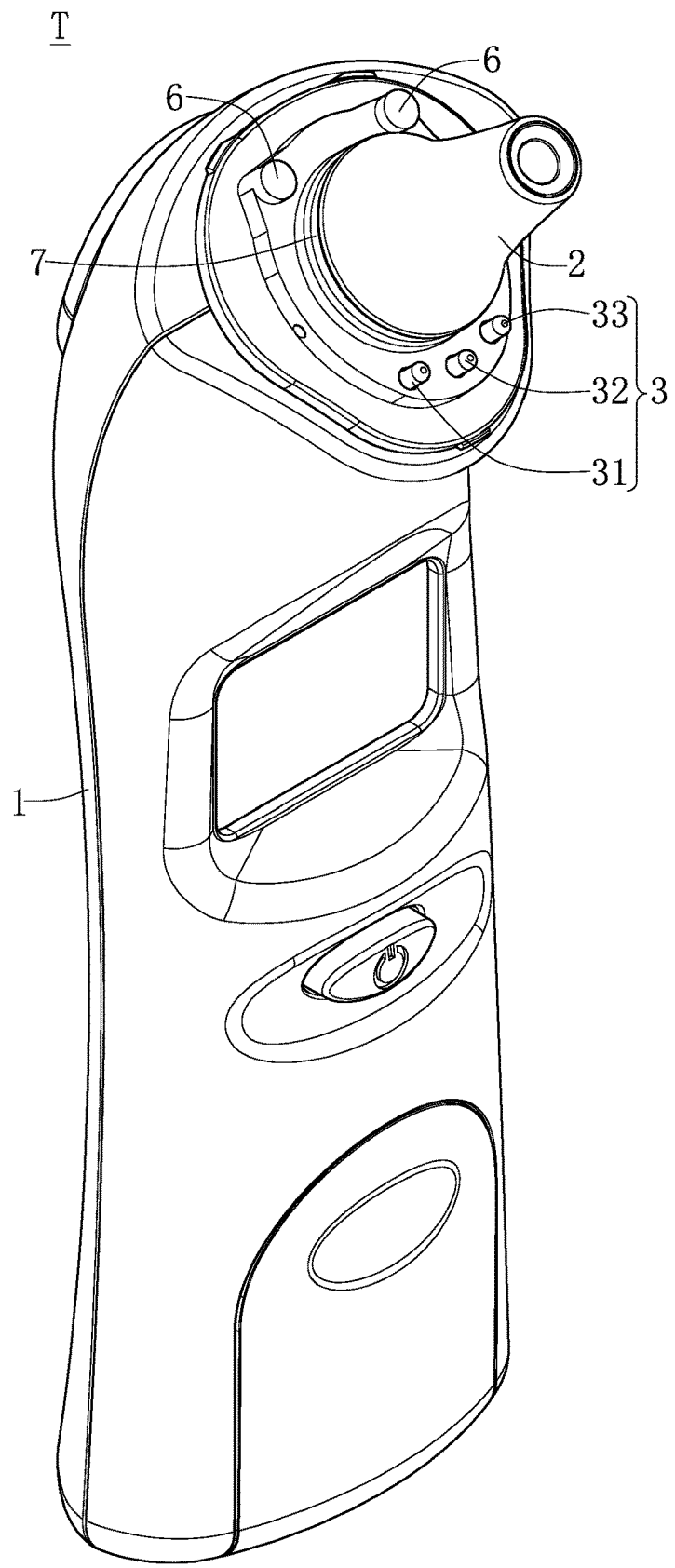
FIG. 1 is a first perspective view of an ear thermometer capable of identifying an infrared transmittance of a probe cover of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Figure 2:
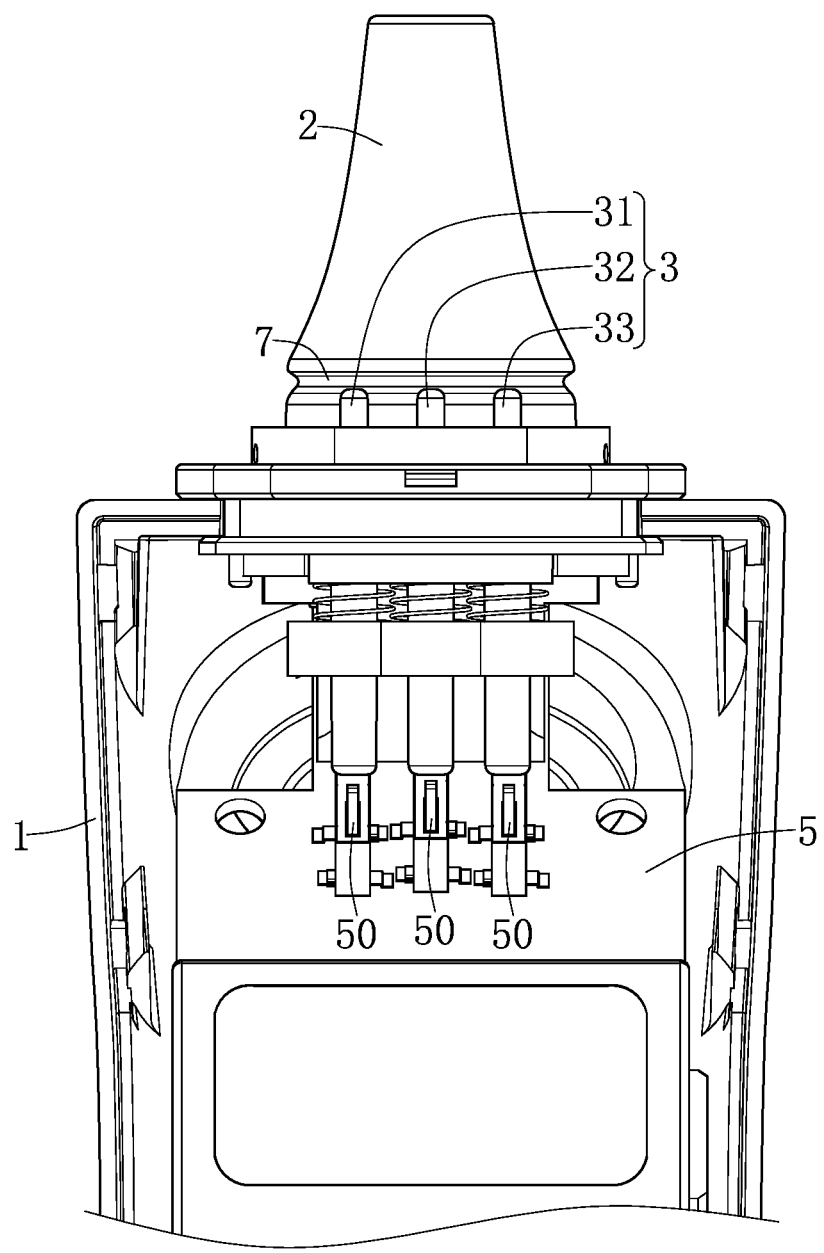
FIG. 2 is a partial cross-sectional view of the ear thermometer capable of identifying the infrared transmittance of the probe cover of the present disclosure.
Figure 3:
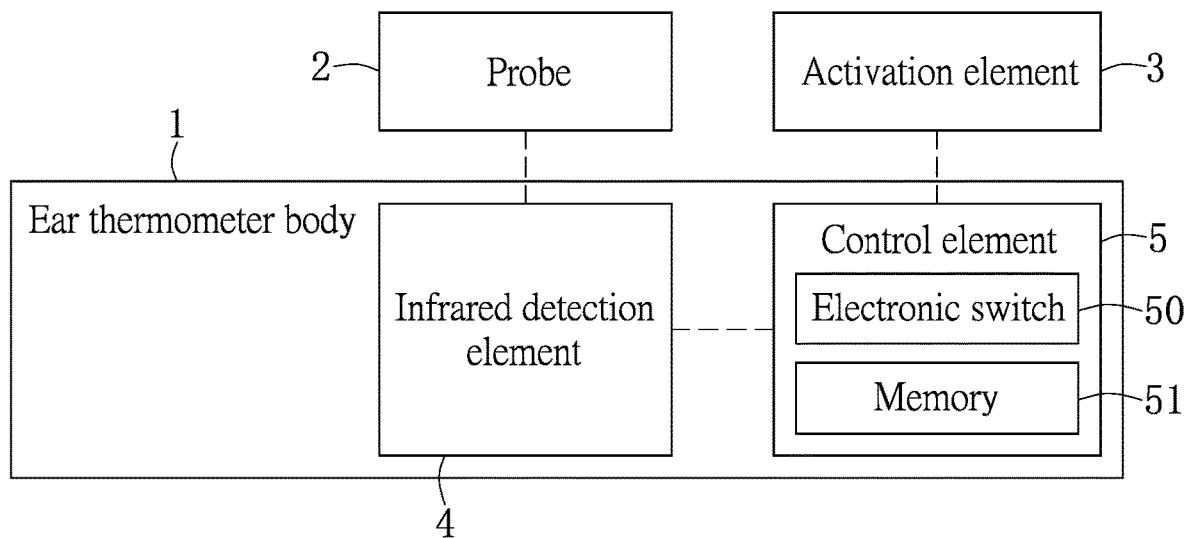
FIG. 3 is a functional block diagram of the ear thermometer capable of identifying the infrared transmittance of the probe cover of the present disclosure.
Figure 4:
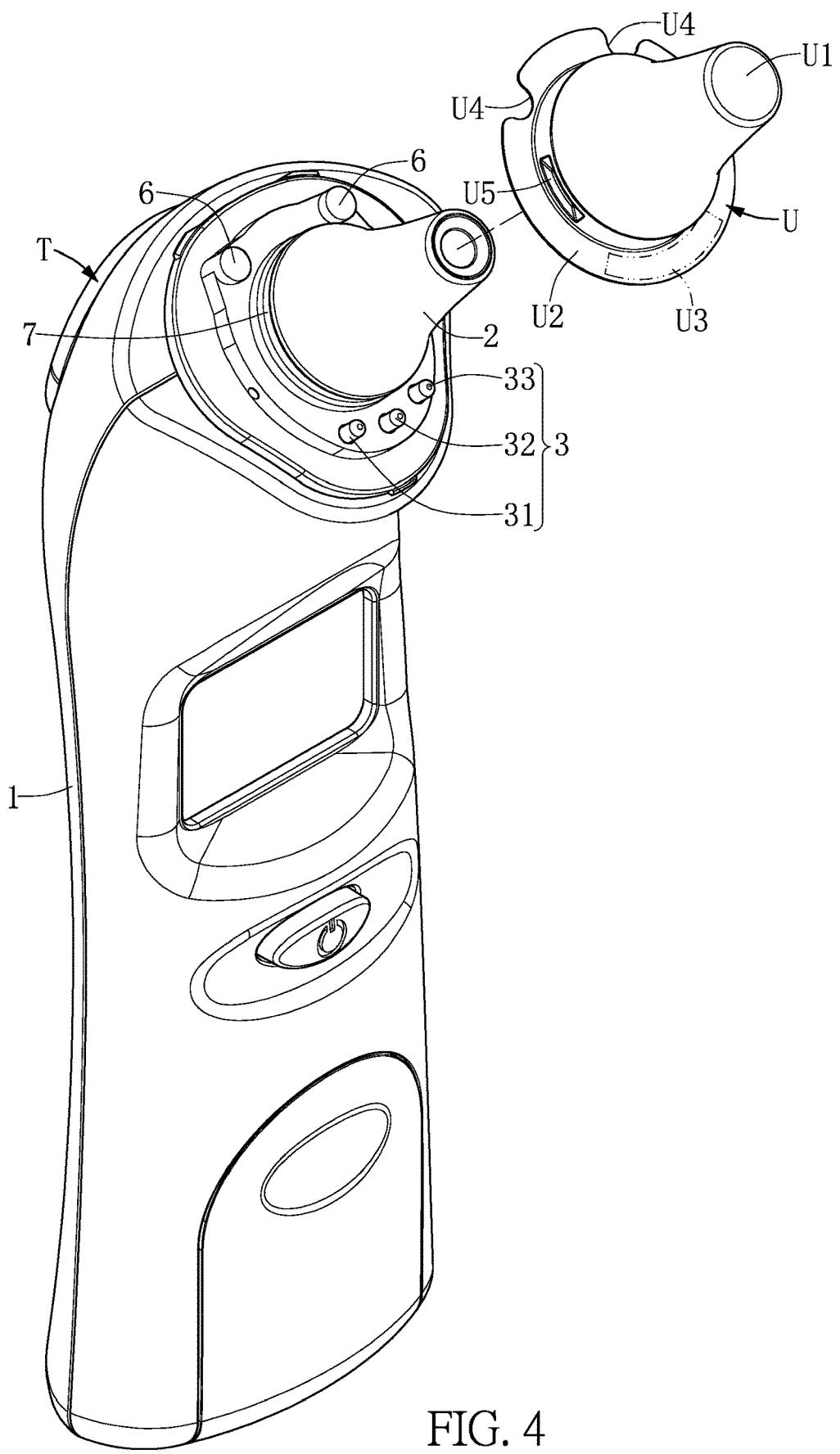
FIG. 4 is a schematic view of the ear thermometer capable of identifying the infrared transmittance of the probe cover and the probe cover of the present disclosure.

References are made to FIG. 1 to FIG. 4, in which FIG. 1 is a first perspective view of an ear thermometer capable of identifying an infrared transmittance of the probe cover of the present disclosure, FIG. 2 is a partial cross-sectional view of the ear thermometer capable of identifying the infrared transmittance of the probe cover of the present disclosure, FIG. 3 is a functional block diagram of the ear thermometer capable of identifying the infrared transmittance of the probe cover of the present disclosure, and FIG. 4 is a schematic view of the ear thermometer capable of identifying the infrared transmittance of the probe cover and the probe cover of the present disclosure. The present disclosure provides an ear thermometer T capable of identifying an infrared transmittance of a probe cover U, the ear thermometer T includes an ear thermometer body 1, a probe 2, and a plurality of activation elements 3. The probe 2 is disposed on the ear thermometer body 1 and can allow a probe cover U to be placed thereon. The probe cover U has a closed end U1 that is penetrable by infrared rays, and that is where the infrared rays mainly pass through). Therefore, the closed end U1 has a thickness and different infrared transmittances according to thickness variations thereof. For the probe cover U, the infrared transmittance thereof actually refers to the infrared transmittance of the closed end U1.

Therefore, the infrared transmittance of the probe cover U varies according to the thickness variations of the closed end U1.

A plurality of activation elements 3 are disposed on the ear thermometer body 1 and adjacent to the probe 2. The activation elements 3 are configured to detect the infrared transmittance of the probe cover U. Furthermore, each of the activation elements 3 includes an ON state and an OFF state so that the activation elements 3 are arranged to form a plurality of different sensor combinations. The different sensor combinations respectively correspond to different infrared transmittances, and any two of the different sensor combinations have two corresponding infrared transmittances that are different from one another.

Furthermore, since the probe cover U provided in the present disclosure is placed on the probe 2 of the ear thermometer T, a flange U2 of the probe cover U can have a plurality of detection positions U3 corresponding to the activation elements 3 of the ear thermometer T. When the probe cover U is placed on the probe 2 of the ear thermometer T, the activation elements 3 can contact the detection positions U3 on the flange U2 of the probe cover U so as to detect the infrared transmittance of the probe cover U. That is to say, the activation elements 3 can detect the infrared transmittances of different probe covers U through the different sensor combinations that are arranged to form the detection positions U3 on the flange U2 of the probe cover U.

Moreover, the ear thermometer T further includes at least one protrusion 6. The protrusion 6 is disposed on the ear thermometer body and adjacent to the probe 2. In the present disclosure, a quantity of the protrusion 6 is two, but the present disclosure is not limited thereto. The ear thermometer T of the present disclosure uses the protrusion 6 to engage with a recessed portion U4 on the flange U2 of the probe cover U, so that the activation elements 3 on the ear thermometer T correspond to the detection positions U3 on the flange U2 of the probe cover U. Through the design of the protrusion 6, when the probe cover U is placed on the probe 2 of the ear thermometer T, a situation where the detection positions U3 are misaligned with the activation elements 3 due to the rotation of the probe cover U can be avoided. In addition, the probe 2 has a groove 7 which surrounds an outer surface of the probe 2. A structure of the groove 7 is designed so as to allow the groove 7 to engage with an abutting portion U5 of the probe cover U. More specifically, the probe cover U can be fastened (or secured) in the groove 7 of the probe 2 through the abutting portion U5, so that the probe cover U is fixed on the probe 2 of the ear thermometer T. It is worth noting that the probe cover U provided in the present embodiment of the present disclosure can be an integrally-formed hard ear cap.

It is also worth noting that in the next embodiment of the present disclosure, the activation elements 3 can be elastic and pressable mechanical pins. The ON state of each of the activation elements 3 is a pin in a pressed state, and the OFF state of each of the activation elements 3 is a pin in an unpressed state. That is to say, when the probe cover U is placed on the probe 2 of the ear thermometer T, the activation elements 3 on the ear thermometer T can be in the pressed state or the unpressed state based on whether or not there are holes on the detection positions U3 on the flange U2 of the probe cover U, so that the activation elements 3 do not trigger a sensing signal or trigger at least one sensing signal. The specific process of the activation elements 3 triggering the sensing signal will be described later in detail, but the present disclosure is not limited thereto. However, in other embodiments of the present disclosure, the ON state and the OFF state of the activation elements 3 can be in other forms. For example, the activation elements 3 can be optoelectronic switches (optoelectronic sensors) that use a translucence/opaqueness of the detection positions U3 on the flange U2 of the probe cover U to block a light beam emitted by the optoelectronic switch, or allow the light beam to pass through, so as to detect the infrared transmittance of the probe cover U. The ON state of the activation elements 3 is a state in which the light beam emitted by the optoelectronic switch is blocked, and the OFF state of the activation elements 3 is a state in which the light beam emitted by the optoelectronic switch is not blocked.

The ear thermometer T further includes an infrared detection element 4 and a control element 5. The infrared detection element 4 is disposed in the ear thermometer body 1. When the probe cover U is placed on the probe 2 of the ear thermometer T, the infrared ray can pass through the probe cover U and enter the ear thermometer body 1 through the probe 2. The control element 5 is disposed in the ear thermometer body 1. When each of the activation elements 3 is in the ON state (that is, a pin is in the pressed state), each of the activation elements 3 can trigger the sensing signal to be sent to the control element 5. Therefore, the different sensor combinations formed by the activation elements 3 (for example, one of the activation elements 3 is in the ON state, and another one of the activation elements 3 is in the OFF state) cannot trigger the sensing signal or trigger the at least one sensing signal to be sent to the control element 5. The control element 5 can identify the infrared transmittance of the probe cover U according to a received sensing signal (or by not receiving a sensing signal).

Next, the operating principle of the ear thermometer T is further described. The infrared rays entering the ear thermometer body 1 can be received by the infrared detection element 4 and be output as a detection signal S 1. It should be noted that the infrared rays referred to herein are mainly infrared rays emitted from a human body. The control element 5 is electrically connected to the infrared detection element 4, such that the control element 5 can receive the detection signal and convert it into an initial temperature value. The control element 5 can be, for example, a central processing unit (CPU) or a microcontroller (MCU) that is commonly found in electronic devices, but the present disclosure is not limited thereto. The control element 5 includes a plurality of electronic switches 50 and a memory 51. A quantity of the electronic switches 50 is configured corresponding to a quantity of the activation elements 3, and the electronic switches 50 are respectively located below the activation elements 3. When one of the activation elements 3 on the ear thermometer T is pressed down, the one of the activation elements 3 can press down to a corresponding one of the electronic switches 50 below the one of the activation elements 3 so as to contact the corresponding one of the electronic switches 50, and the corresponding one of the electronic switches 50 can send the sensing signal, that is, the at least one sensing signal triggered by the activation elements 3 as previously mentioned. The memory 51 stores a plurality of preset infrared transmittance values and an infrared transmittance calibration parameter. The control element 5 compensates and calibrates the measured initial temperature value according to the preset infrared transmittance values and the infrared transmittance calibration parameter, and according to the infrared transmittances of the probe cover U measured by the activation elements 3, so as to obtain a calibrated temperature value.

First Embodiment

Figure 5:
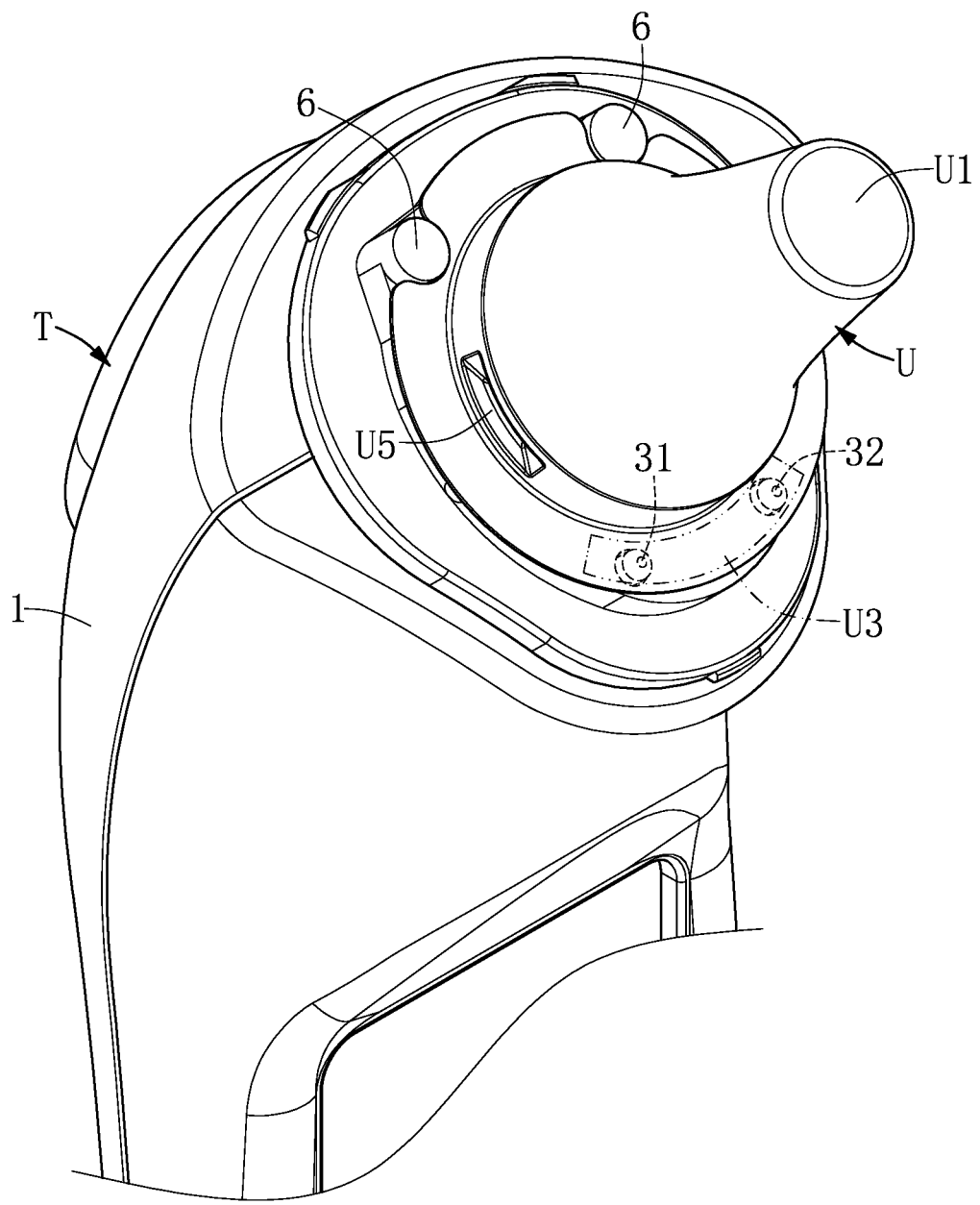
FIG. 5 is a schematic view of a first sensor combination of activation elements of the ear thermometer capable of identifying the infrared transmittance of the probe cover according to a first embodiment of the present disclosure.
Figure 6:
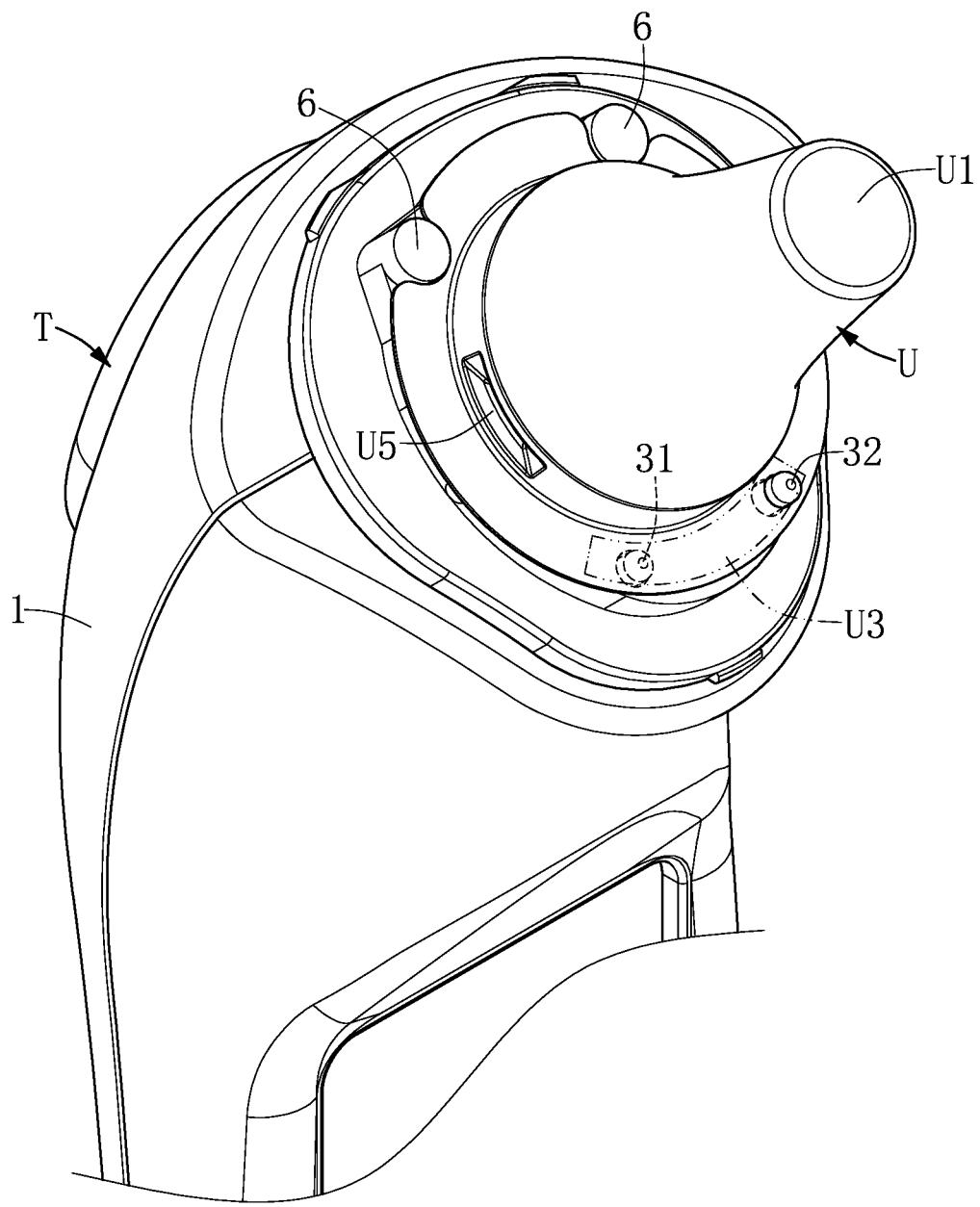
FIG. 6 is a schematic view of a second sensor combination of the activation element of the ear thermometer capable of identifying the infrared transmittance of the probe cover according to the first embodiment of the present disclosure.
Figure 7:
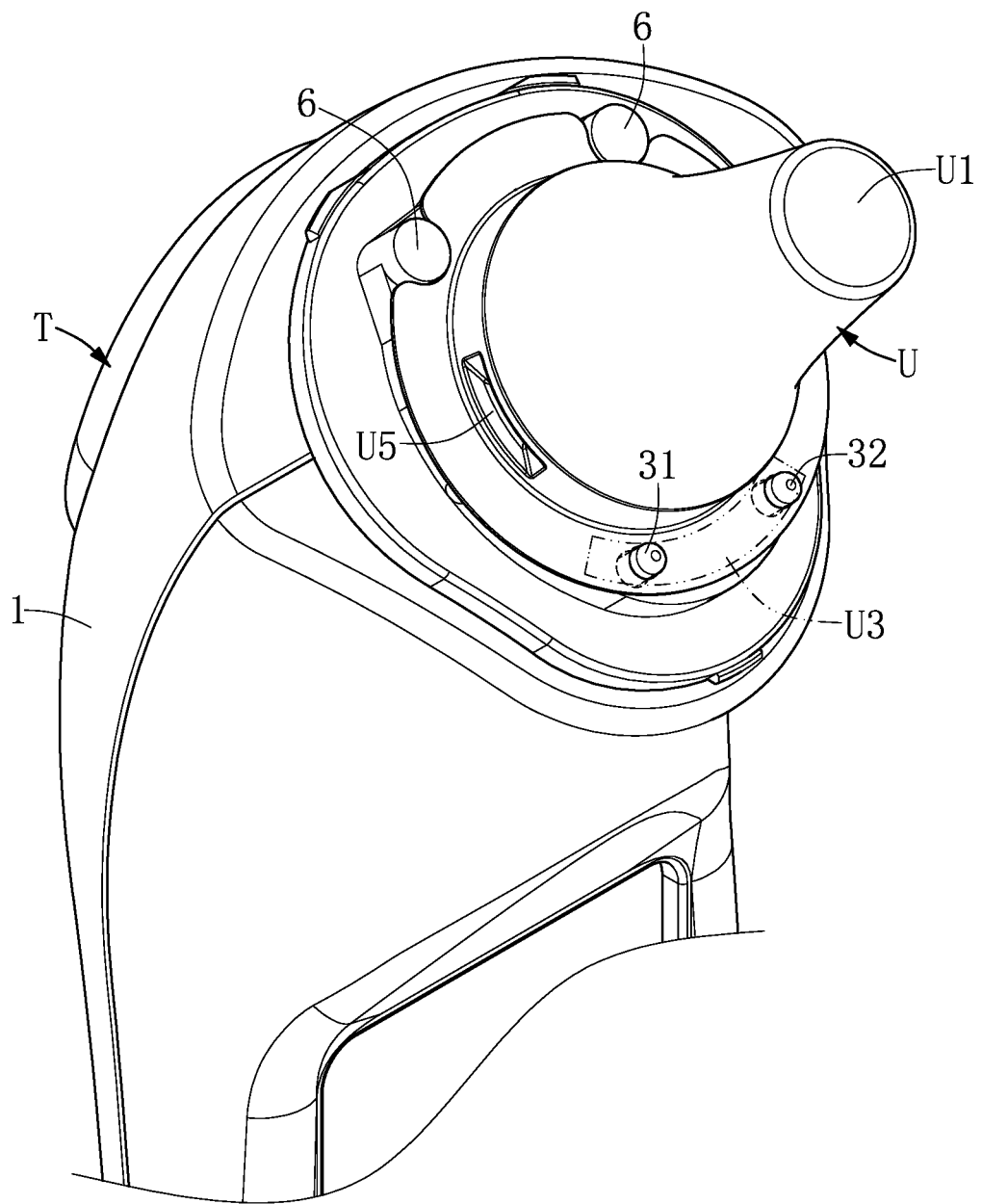
FIG. 7 is a schematic view of a third sensor combination of the activation element of the ear thermometer capable of identifying the infrared transmittance of the probe cover according to the first embodiment of the present disclosure.

Referring to FIG. 5 to FIG. 7, the specific features of the activation elements 3 on the ear thermometer T provided by a first embodiment of the present disclosure will be further described. In this embodiment, a quantity of the activation elements 3 is set to be two, and a quantity of the sensor combinations is set to be three. Two of the activation elements 3 are divided into a first activation element 31 and a second activation element 32, and three sensor combinations are divided into a first sensor combination, a second sensor combination, and a third sensor combination. In addition, it should be noted that since each of the activation elements 3 can either be in the ON state or the OFF state, the two activation elements 3 in this embodiment can have up to four sensor combinations. However, an actual quantity of the sensor combinations used can be adjusted according to user requirements, and the present disclosure is not limited to the above-mentioned examples.

As shown in FIG. 5, FIG. 5 is a schematic view of the first sensor combination of activation elements of the ear thermometer capable of identifying the infrared transmittance of the probe cover according to the first embodiment of the present disclosure. The first sensor combination refers to the first activation element 31 and the second activation element 32 in the ON state. In detail, in the first sensor combination, the first activation element 31 on the ear thermometer T is in the ON state, that is, the first activation element 31 is a pin in a pressed state, and the second activation element 32 on the ear thermometer T is also in the ON state, that is, the second activation element 32 is also a pin in a pressed state. In other words, the two activation elements 3 on the ear thermometer T are both pins in the pressed state. In addition, the infrared transmittance of the probe cover U corresponding to the first sensor combination is set to be 80%+/−1%. That is to say, when the probe cover U is placed on the probe 2 of the ear thermometer T, the two activation elements 3 can respectively contact the two detection positions U3 on the flange U2 of the probe cover U, and the two activation elements 3 are respectively pressed down by the two detection positions U3 so that the activation elements 3 can detect the infrared transmittance of the probe cover U as 80%+/−1%.

As shown in FIG. 6, FIG. 6 is a schematic view of the second sensor combination of the activation element of the ear thermometer capable of identifying the infrared transmittance of the probe cover according to the first embodiment of the present disclosure. The second sensor combination refers to the first activation element 31 in the ON state and the second activation element 32 in the OFF state. In detail, in the second sensor combination, the first activation element 31 on the ear thermometer T is in the ON state, that is, the first activation element 31 is a pin in a pressed state, and the second activation element 32 on the ear thermometer T is in the OFF state, that is, the second activation element 32 is a pin in an unpressed state. In other words, only one of the two activation elements 3 on the ear thermometer T is a pin in the pressed state. In addition, the infrared transmittance of the probe cover U corresponding to the second sensor combination is set to be 79.5%+/−1%. That is to say, when the probe cover U is placed on the probe 2 of the ear thermometer T, the two activation elements 3 can respectively contact the two detection positions U3 on the flange U2 of the probe cover U, and the first activation element 31 of the two activation elements 3 is pressed down by the two detection positions U3 so that the activation elements 3 can detect the infrared transmittance of the probe cover U as 79.5%+/−1%.

As shown in FIG. 7, FIG. 7 is a schematic view of a third sensor combination of the activation element of the ear thermometer capable of identifying the infrared transmittance of the probe cover according to the first embodiment of the present disclosure. The third sensor combination refers to the first activation element 31 and the second activation element 32 in the OFF state. In detail, in the third sensor combination, the first activation element 31 on the ear thermometer T is in the OFF state, that is, the first activation element 31 is a pin in an unpressed state, and the second activation element 32 on the ear thermometer T is also in the OFF state, that is, the second activation element 32 is also a pin in an unpressed state. In other words, the two activation elements 3 on the ear thermometer T are both pins in the unpressed state. In addition, the infrared transmittance of the probe cover U corresponding to the third sensor combination is set to be 80.5%+/−1%. That is to say, when the probe cover U is placed on the probe 2 of the ear thermometer T, the two activation elements 3 can respectively contact the two detection positions U3 on the flange U2 of the probe cover U, and the two activation elements 3 are not pressed down by the two detection positions U3 so that the activation elements 3 can detect the infrared transmittance of the probe cover U as 80.5%+/−1%.

In addition, it should be noted that the above-mentioned infrared transmittance of the probe cover U corresponding to each of the sensor combination is set according to user requirements, and the present disclosure is not limited thereto. Therefore, in other embodiments, the infrared transmittances of the probe cover U corresponding to the first sensor combination, the second sensor combination, and the third sensor combination do not have to be 80%, 79.5%, and 80.5% (i.e., being the same as those mentioned in the present embodiment), but can also be other values, such as 81%, 80%, and 79%.

Second Embodiment

Referring to FIG. 8 to FIG. 12, the specific features of the activation elements 3 on the ear thermometer T provided by a second embodiment of the present disclosure will be further described. In this embodiment, a quantity of the activation elements 3 is set to be three, and a quantity of the sensor combinations is set to be five. Three activation elements 3 are divided into a first activation element 31, a second activation element 32, and a third activation element 33, and five sensor combinations are divided into a first sensor combination, a second sensor combination, a third sensor combination, a fourth sensor combination, and a fifth sensor combination. In addition, it should be noted that since each of the activation elements 3 can either be in the ON state or the OFF state, the three activation elements 3 in this embodiment can have up to eight sensor combinations. However, an actual quantity of the sensor combinations used can be adjusted according to user requirements, and the present disclosure is not limited to the above-mentioned examples.

Figure 8:
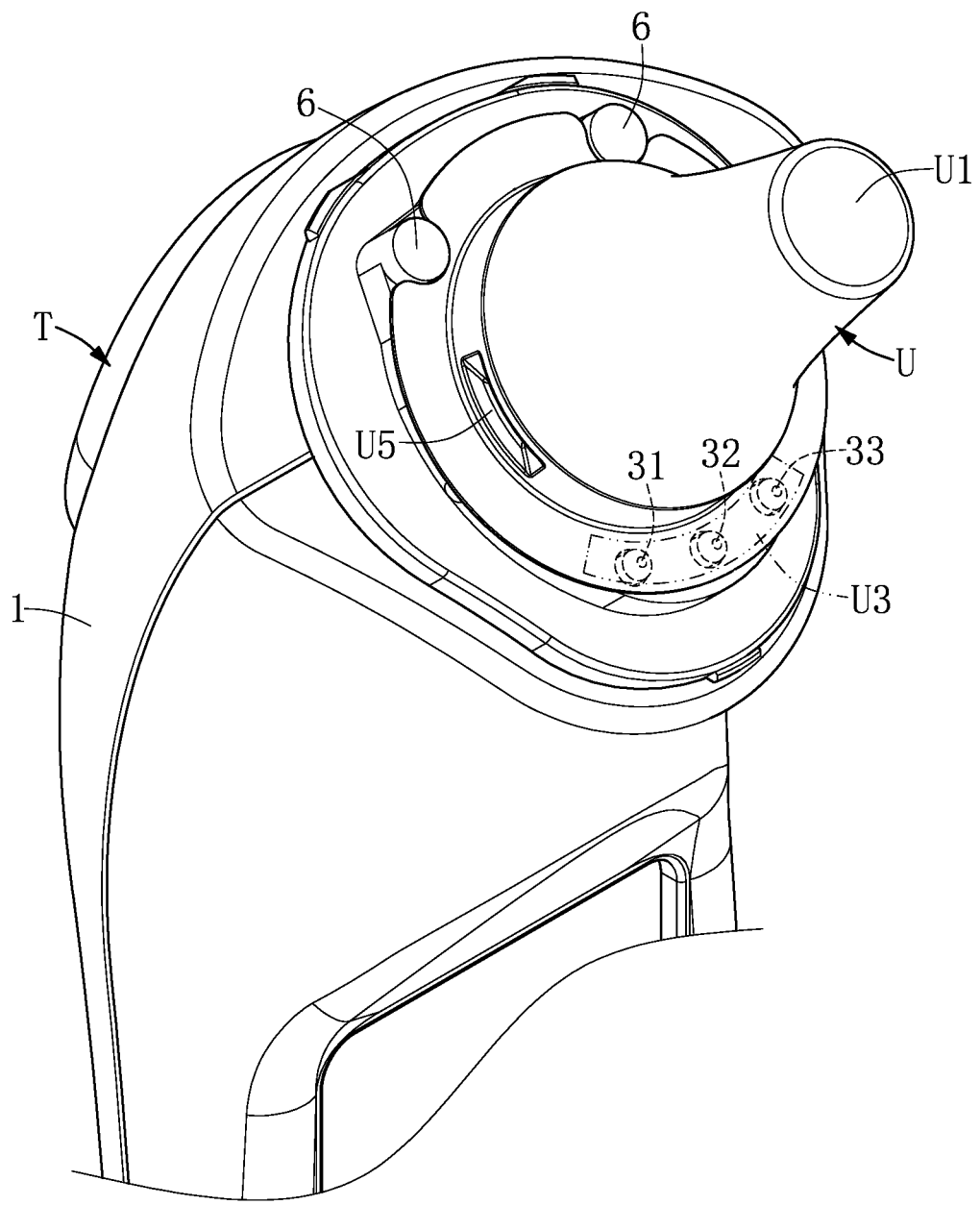
FIG. 8 is a schematic view of a first sensor combination of activation elements of the ear thermometer capable of identifying the infrared transmittance of the probe cover according to a second embodiment of the present disclosure.

As shown in FIG. 8, FIG. 8 is a schematic view of a first sensor combination of activation elements of the ear thermometer capable of identifying the infrared transmittance of the probe cover according to a second embodiment of present disclosure. The first sensor combination refers to the first activation element 31, the second activation element 32, and the third activation element 33 in the ON state. In detail, in the first sensor combination, the first activation element 31 on the ear thermometer T is in the ON state, that is, the first activation element 31 is a pin in a pressed state, the second activation element 32 on the ear thermometer T is also in the ON state, that is, the second activation element 32 is also a pin in a pressed state, and the third activation element 33 is again in the ON state, that is, the third activation element 33 is again a pin in a pressed state. In other words, the three activation elements 3 on the ear thermometer T are all pins in the pressed state. In addition, the infrared transmittance of the probe cover U corresponding to the first sensor combination is set to be 80%+/−1%. That is to say, when the probe cover U is placed on the probe 2 of the ear thermometer T, the three activation elements 3 can respectively contact the three detection positions U3 on the flange U2 of the probe cover U, and the three activation elements 3 (the first activation element 31, the second activation element 32, and the third activation element 33) are respectively pressed down by the three detection positions U3 so that the activation elements 3 can detect the infrared transmittance of the probe cover U as 80%+/−1%.

Figure 9:
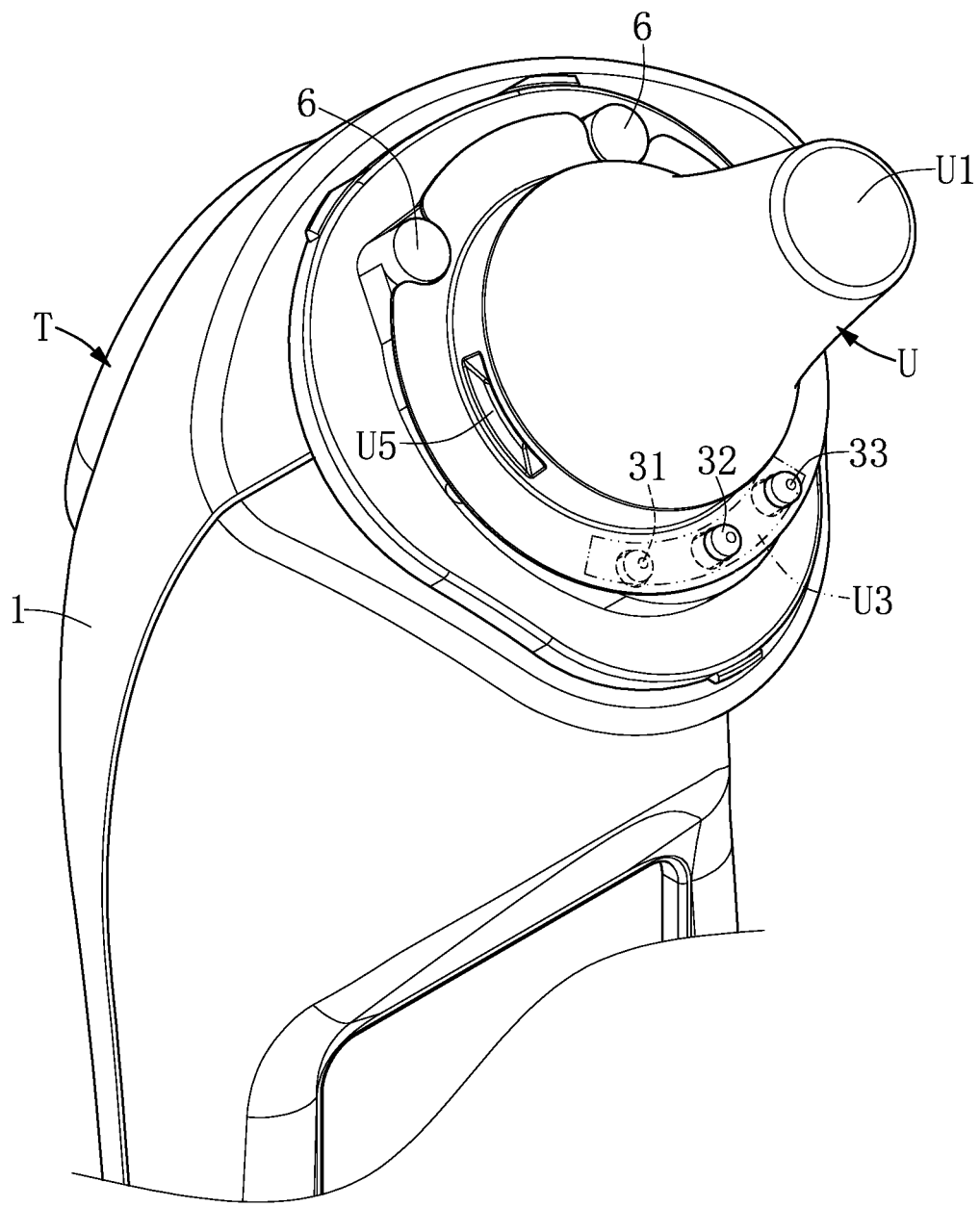
FIG. 9 is a schematic view of a second sensor combination of the activation element of the ear thermometer capable of identifying the infrared transmittance of the probe cover according to the second embodiment of the present disclosure.

As shown in FIG. 9, FIG. 9 is a schematic view of a second sensor combination of the activation element of the ear thermometer capable of identifying the infrared transmittance of the probe cover according to the second embodiment of the present disclosure. The second sensor combination refers to the first activation element 31 in the ON state, and the second activation element 32 and the third activation element 33 in the OFF state. In detail, in the second sensor combination, the first activation element 31 on the ear thermometer T is in the ON state, that is, the first activation element 31 is a pin in a pressed state, the second activation element 32 on the ear thermometer T is in the OFF state, that is, the second activation element 32 is a pin in an unpressed state, and the third activation element 33 on the ear thermometer T is also in the OFF state, that is, the third activation element 33 is also a pin in an unpressed state. In other words, only one of the three activation elements 3 on the ear thermometer T is a pin in the pressed state. In addition, the infrared transmittance of the probe cover U corresponding to the second sensor combination is set to be 80.5%+/−1%. That is to say, when the probe cover U is placed on the probe 2 of the ear thermometer T, the three activation elements 3 can respectively contact the three detection positions U3 on the flange U2 of the probe cover U, and the first activation element 31 of the three activation elements 3 is pressed down by the three detection positions U3 so that the activation elements 3 can detect the infrared transmittance of the probe cover U as 80.5%+/−1%.

Figure 10:
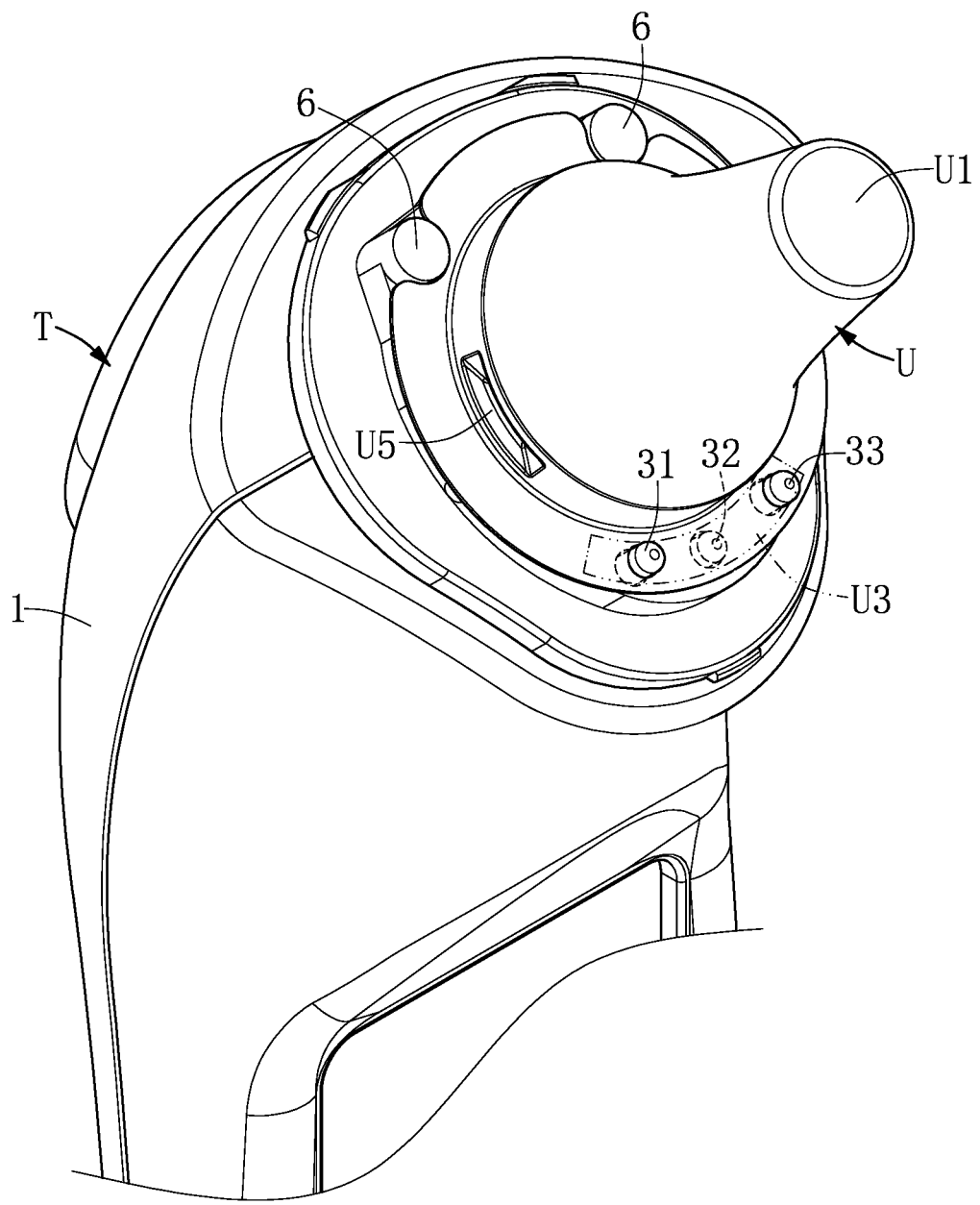
FIG. 10 is a schematic view of a third sensor combination of the activation element of the ear thermometer capable of identifying the infrared transmittance of the probe cover according to the second embodiment of the present disclosure.

As shown in FIG. 10, FIG. 10 is a schematic view of a third sensor combination of the activation element of the ear thermometer capable of identifying the infrared transmittance of the probe cover according to the second embodiment of the present disclosure. The third sensor combination refers to the second activation element 32 in the ON state, and the first activation element 31 and the third activation element 33 in the OFF state. In detail, in the third sensor combination, the first activation element 31 on the ear thermometer T is in the OFF state, that is, the first activation element 31 is a pin in an unpressed state, the second activation element 32 on the ear thermometer T is in the ON state, that is, the second activation element 32 is a pin in a pressed state, and the third activation element 33 on the ear thermometer T is in the OFF state, that is, the third activation element 33 is a pin in an unpressed state. In other words, only one of the three activation elements 3 on the ear thermometer T is a pin in the pressed state. In addition, the infrared transmittance of the probe cover U corresponding to the third sensor combination is set to be 81%+/−1%. That is to say, when the probe cover U is placed on the probe 2 of the ear thermometer T, the three activation elements 3 can respectively contact the three detection positions U3 on the flange U2 of the probe cover U, and the second activation element 32 of the three activation elements 3 is pressed down by the three detection positions U3 so that the activation elements 3 can detect the infrared transmittance of the probe cover U as 81%+/−1%.

Figure 11:
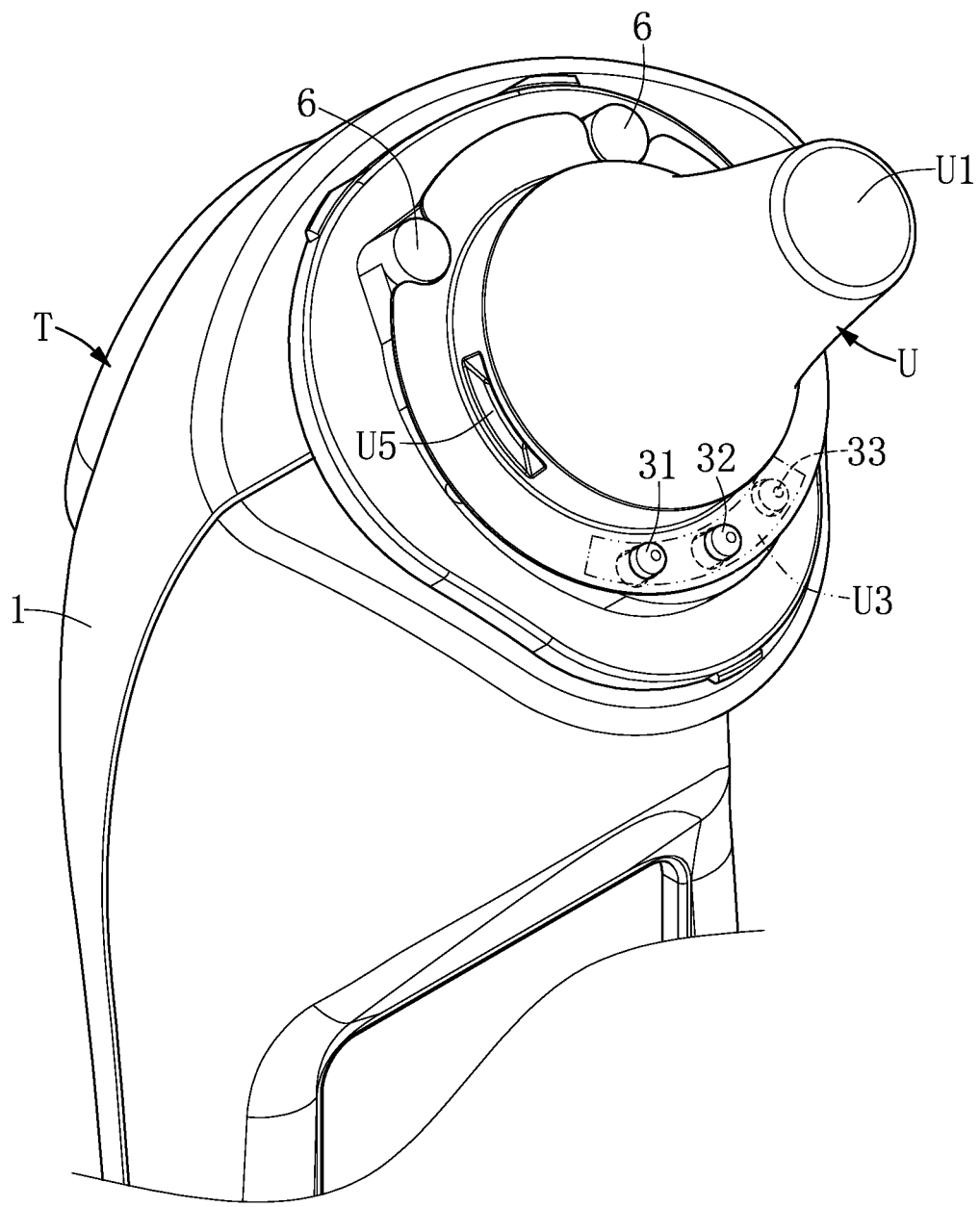
FIG. 11 is a schematic view of a fourth sensor combination of the activation element of the ear thermometer capable of identifying the infrared transmittance of the probe cover according to the second embodiment of the present disclosure.

As shown in FIG. 11, FIG. 11 is a schematic view of a fourth sensor combination of the activation element of the ear thermometer capable of identifying the infrared transmittance of the probe cover according to the second embodiment of the present disclosure. The fourth sensor combination refers to the third activation element 33 in the ON state, and the first activation element 31 and the second activation element 32 in the OFF state. In detail, in the fourth sensor combination, the first activation element 31 on the ear thermometer T is in the OFF state, that is, the first activation element 31 is a pin in an unpressed state, the second activation element 32 on the ear thermometer T is also in the OFF state, that is, the second activation element 32 is also a pin in an unpressed state, and the third activation element 33 on the ear thermometer T is in an ON state, that is, the third activation element 33 is a pin in a pressed state. In other words, only one of the three activation elements 3 on the ear thermometer T is a pin in the pressed state. In addition, the infrared transmittance of the probe cover U corresponding to the fourth sensor combination is set to be 79.5%+/−1%. That is to say, when the probe cover U is placed on the probe 2 of the ear thermometer T, the three activation elements 3 can respectively contact the three detection positions U3 on the flange U2 of the probe cover U, and the third activation element 33 of the three activation elements 3 is pressed down by the three detection positions U3 so that the activation elements 3 can detect the infrared transmittance of the probe cover U as 79.5%+/−1%.

Figure 12:
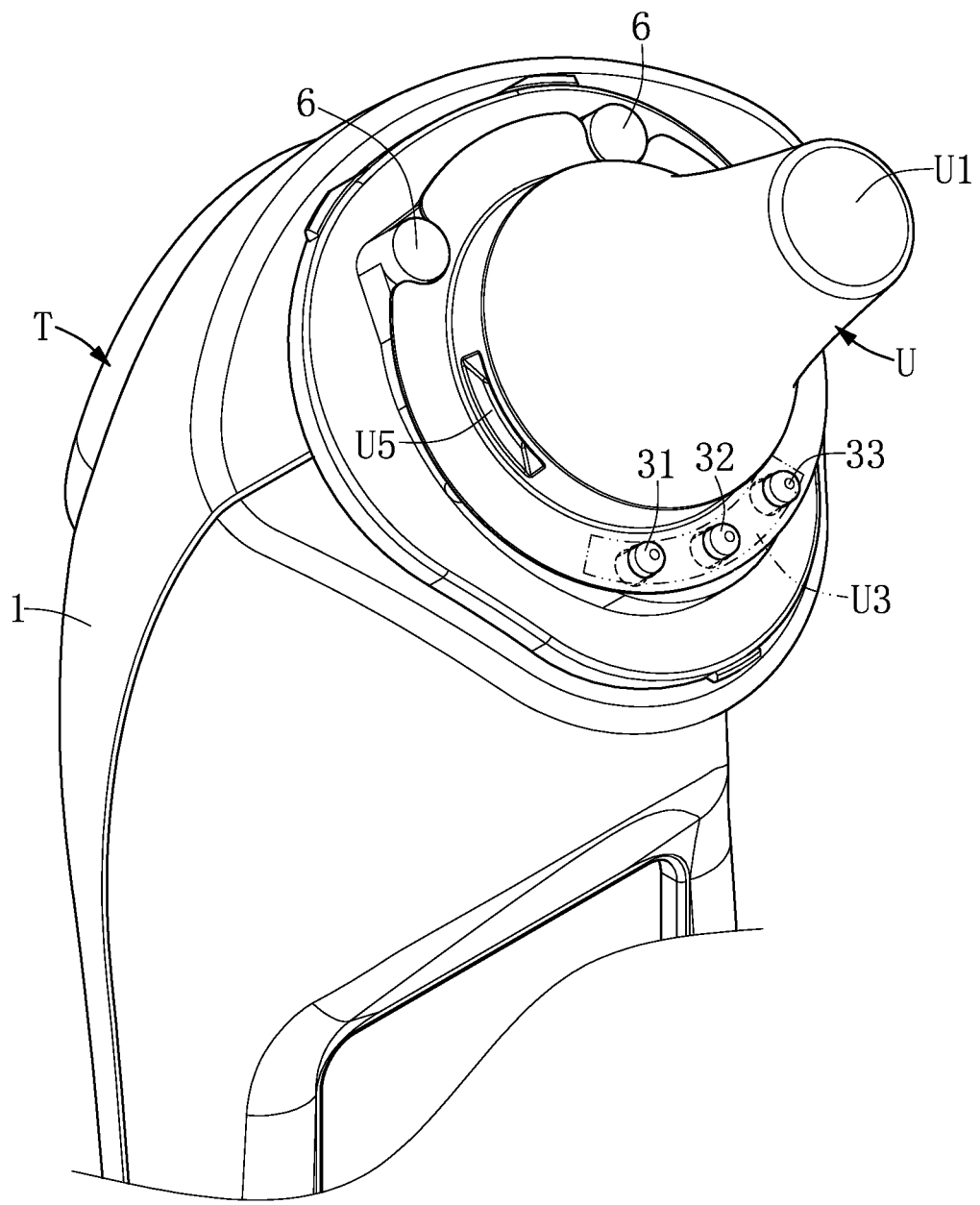
FIG. 12 is a schematic view of a fifth sensor combination of the activation element of the ear thermometer capable of identifying the infrared transmittance of the probe cover according to the second embodiment of the present disclosure.

As shown in FIG. 12, FIG. 12 is a schematic view of a fifth sensor combination of the activation element of the ear thermometer capable of identifying the infrared transmittance of the probe cover according to the second embodiment of the present disclosure. The fifth sensor combination refers to the first activation element 31, the second activation element 32, and the third activation element 33 in the OFF state. In detail, in the fifth sensor combination, the first activation element 31 on the ear thermometer T is in the OFF state, that is, the first activation element 31 is a pin in an unpressed state, the second activation element 32 on the ear thermometer T is also in the OFF state, that is, the second activation element 32 is also a pin in an unpressed state, and the third activation element 33 on the ear thermometer T is again in an OFF state, that is, the third activation element 33 is again a pin in an unpressed state. In other words, the three activation elements 3 on the ear thermometer T are pins in the unpressed state. In addition, the infrared transmittance of the probe cover U corresponding to the fifth sensor combination is set to be 79%+/−1%. That is to say, when the probe cover U is placed on the probe 2 of the ear thermometer T, the three activation elements 3 can respectively contact the three detection positions U3 on the flange U2 of the probe cover U, and any one of the three activation elements 3 (the first activation element 31, the second activation element 32, and the third activation element 33) is not pressed down by the three detection positions U3 so that the activation elements 3 can detect the infrared transmittance of the probe cover U as 79%+/−1%.

In addition, it should be noted that the above-mentioned infrared transmittance of the probe cover U corresponding to each of the sensor combinations is set according to the user requirements, and the present disclosure is not limited thereto. Therefore, in other embodiments, the infrared transmittance of the probe cover U corresponding to the first sensor combination, the second sensor combination, the third sensor combination, the fourth sensor combination, and the fifth sensor combination do not have to be 80%, 80.5%, 81%, 79.5%, and 79% (i.e., being the same as those mentioned in the present embodiment), but can also be other values, such as 82%, 81%, 80%, 79%, and 78%.

Beneficial Effects of the Embodiments

In conclusion, one of the beneficial effects of the present disclosure is that, in the ear thermometer T capable of identifying the infrared transmittance of the probe cover U provided herein, through the technical solutions of "the plurality of activation elements 3 being disposed on the ear thermometer body 1 and being able to detect the infrared transmittance of the probe cover U" and "each of the activation elements 3 including the ON state and the OFF state so that the activation elements 3 being arranged to form a plurality of different sensor combinations, and the different sensor combinations respectively corresponding to a plurality of different infrared transmittances", the ear thermometer T can quickly identify the infrared transmittance of the probe cover U that is placed thereon.

Furthermore, the ear thermometer T uses the protrusion 6 to engage with the recessed portion U4 on the flange U2 of the probe cover U, so that when the probe cover U is placed on the probe 2 of the ear thermometer T, a situation where the detection positions U3 are misaligned with the activation elements 3 due to the rotation of the probe cover U can be avoided.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. An ear thermometer capable of identifying an infrared transmittance of a probe cover, comprising:
    an ear thermometer body;
    a probe being disposed on the ear thermometer body and allowing the probe cover to be placed thereon, wherein the probe cover has a closed end that is penetrable by infrared rays, and the probe cover has different infrared transmittances according to thickness variations of the closed end;
    a plurality of activators disposed on the ear thermometer body and adjacent to the probe, and the plurality of activators are configured to detect the different infrared transmittance of the probe cover; and an infrared detector disposed in the ear thermometer body, wherein the infrared rays pass through the probe cover and enter the ear thermometer body through the probe, and the infrared detector receives the infrared rays and outputs a detection signal;

wherein each of the plurality of activators includes an ON state and an OFF state so that the plurality of activators are arranged to form a plurality of different sensor combinations;

wherein the plurality of different sensor combinations respectively correspond to the different infrared transmittances, and any two of the plurality of different sensor combinations have two corresponding infrared transmittances of the different infrared transmittances that are different from one another;

wherein each of the plurality of activators is a mechanical pin, the ON state of the plurality of activators is the mechanical pin being in a pressed state, and the OFF state of the plurality of activators is the mechanical pin being in an unpressed state.

2. The ear thermometer according to claim 1, further comprising a control element disposed in the ear thermometer body, wherein the control element includes a plurality of electronic switches, and the plurality of electronic switches are respectively located below the plurality of activators, wherein, when one of the plurality of activators is in the ON state, the one of the plurality of activators is pressed down to contact a corresponding one of the plurality of electronic switches.

3. The ear thermometer according to claim 2, wherein the control element is electrically connected to the infrared detector, and the control element receives and converts the detection signal into an initial temperature value, wherein the control element further includes a memory, the memory stores a plurality of preset infrared transmittance values and an infrared transmittance calibration parameter, the control element compensates and calibrates the measured initial temperature value according to the plurality of preset infrared transmittance values and the infrared transmittance calibration parameter, and according to the different infrared transmittances of the probe cover detected by the plurality of activators, so as to obtain a calibrated temperature value.

4. The ear thermometer according to claim 1, wherein the probe further has a groove, and the groove surrounds an outer surface of the probe.

5. The ear thermometer according to claim 1, wherein, when a quantity of the plurality of activators is set to be two, a quantity of the plurality of different sensor combinations is set to be at most four.

6. The ear thermometer according to claim 1, wherein, when a quantity of the plurality of activators is set to be three, a quantity of the plurality of different sensor combinations is set to be at most eight.

7. The ear thermometer according to claim 1, further comprising at least one protrusion, the at least one protrusion being disposed on the ear thermometer body and adjacent to the probe, and the at least one protrusion being engaged with a recessed portion on a flange of the probe cover.

8. An ear thermometer capable of identifying an infrared transmittance of a probe cover, comprising:

an ear thermometer body;

a probe being disposed on the ear thermometer body and allowing the probe cover to be placed thereon, wherein the probe cover has a closed end that is penetrable by infrared rays, and the probe cover has different infrared transmittances according to thickness variations of the closed end;

a plurality of activators disposed on the ear thermometer body and adjacent to the probe, and the plurality of activators are configured to detect the different infrared transmittance of the probe cover; and an infrared detector disposed in the ear thermometer body, wherein the infrared rays pass through the probe cover and enter the ear thermometer body through the probe, and the infrared detector receives the infrared rays and outputs a detection signal;

wherein each of the plurality of activators includes an ON state and an OFF state so that the plurality of activators are arranged to form a plurality of different sensor combinations;

wherein the plurality of different sensor combinations respectively correspond to the different infrared transmittances, and any two of the plurality of different sensor combinations have two corresponding infrared transmittances of the different infrared transmittances that are different from one another;

wherein each of the plurality of activators is an optoelectronic switch, and the ON state of the plurality of activators is a state in which a light beam emitted by the optoelectronic switch is blocked, and the OFF state of the plurality of activators is a state in which the light beam emitted by the optoelectronic switch is not blocked.

9. The ear thermometer according to claim 8, further comprising a control element disposed in the ear thermometer body, wherein the control element includes a plurality of electronic switches, and the plurality of electronic switches are respectively located below the plurality of activators, wherein, when one of the plurality of activators is in the ON state, the one of the plurality of activators is pressed down to contact a corresponding one of the plurality of electronic switches.

10. The ear thermometer according to claim 9, wherein the control element is electrically connected to the infrared detector, and the control element receives and converts the detection signal into an initial temperature value, wherein the control element further includes a memory, the memory stores a plurality of preset infrared transmittance values and an infrared transmittance calibration parameter, the control element compensates and calibrates the measured initial temperature value according to the plurality of preset infrared transmittance values and the infrared transmittance calibration parameter, and according to the different infrared transmittances of the probe cover detected by the plurality of activators, so as to obtain a calibrated temperature value.

11. The ear thermometer according to claim 8, wherein the probe further has a groove, and the groove surrounds an outer surface of the probe.

12. The ear thermometer according to claim 8, wherein, when a quantity of the plurality of activators is set to be two, a quantity of the plurality of different sensor combinations is set to be at most four.

13. The ear thermometer according to claim 8, wherein, when a quantity of the plurality of activators is set to be three, a quantity of the plurality of different sensor combinations is set to be at most eight.

14. The ear thermometer according to claim 8, further comprising at least one protrusion, the at least one protrusion being disposed on the ear thermometer body and adjacent to the probe, and the at least one protrusion being engaged with a recessed portion on a flange of the probe cover.

* * * * *